United States Patent [19]
Schwan

[11] 3,946,075
[45] Mar. 23, 1976

[54] 2-AMINOMETHYLENE-1-PHENYL-1,3-BUTANEDIONE

[75] Inventor: Thomas J. Schwan, Norwich, N.Y.

[73] Assignee: Morton-Norwich Products, Inc., Norwich, N.Y.

[22] Filed: Nov. 1, 1974

[21] Appl. No.: 520,023

[52] U.S. Cl. .......... 260/570.5 C; 260/592; 424/330; 424/331
[51] Int. Cl.² ......................................... C07C 97/10
[58] Field of Search .......................... 260/570.5 C

[56] References Cited
UNITED STATES PATENTS 2,240,965  5/1941  Melsen........................ 260/570.5 X

*Primary Examiner*—Robert V. Hines
*Attorney, Agent, or Firm*—Anthony J. Franze

[57] ABSTRACT

Certain 1,3-butanediones of the formula:

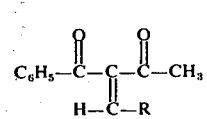

wherein R is ethoxy or amino possess pharmacological activity as depressants and skeletal muscle relaxants.

1 Claim, No Drawings

2-AMINOMETHYLENE-1-PHENYL-1,3-BUTANEDIONE

This invention relates to chemical compounds. In particular it is concerned with compounds of the formula:

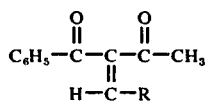

wherein R is ethoxy or amino. These compounds possess pharmacological activity. Thus these compounds, when administered orally to mice in doses ranging from 200–1600 mg/kg suspended in 0.5 percent aqueous methyl cellulose (4000 cps), caused central nervous system depression and skeletal muscle relaxation commencing at two hours post dosing.

These compounds are capable of existing in tautomeric form.

In order that this invention may be readily available to and understood by those skilled in the art the following examples are appended.

EXAMPLE I

2-Ethoxymethylene-1-phenyl-1,3-butanedione

To 200 g (1.23 moles) of benzoylacetone was added 320 g (2.16 moles) of ethyl orthoformate followed by 360 g (3.52 mole) acetic anhydride. The mixture was stirred and refluxed for 3.0 hours and the pot temperature dropped from 120° to 100° during the reflux period. The reflux condenser was removed and the volatile products were distilled at pot temperatures up to 140°. The remaining acetic anhydride and ethyl orthoformate were removed on a rotary evaporator at 100°. The residue crystallized at room temperature and was recrystallized from toluene to give in two crops 206 g (77%) of the product, m.p. 68°–71°.

An analytical sample, m.p. 68–71°, was obtained by recrystallization from toluene.

Anal. Calcd. for $C_{13}H_{14}O_3$: C, 71.54; H, 6.47. Found: C, 71.65; H, 6.47.

EXAMPLE II

2-Aminomethylene-1-phenyl-1,3-butanedione

To a solution of 2.0 g (0.0091 mole) of the compound of Example I in 40 ml methanol was added 10 ml concentrated aqueous ammonia. The solution was stirred at ambient temperature for 15 minutes, then stirred and gently refluxed for 45 minutes. The solvents were stripped and to the residue was added 20 ml absolute ethanol and 10 ml toluene. The solvents were again stripped. The residue was recrystallized from 20 ml of toluene to afford 1.51 g (88%) of the product.

An analytical sample m.p. 93°–96°, was obtained by recrystallization from toluene.

Anal. Calcd. for $C_{11}H_{11}NO_2$: C, 69.82; H, 5.86; N, 7.40. Found: C, 69.45; H, 5.84; N, 7.41.

What is claimed is:

What is claimed is:

1. The compound 2-aminomethylene-1-phenyl-1,3-butanedione.

* * * * *